United States Patent
Kull et al.

(10) Patent No.: US 10,377,716 B2
(45) Date of Patent: *Aug. 13, 2019

(54) COMPOSITION AND METHOD FOR PREVENTION, MITIGATION OR TREATMENT OF AN ENTEROPATHOGENIC BACTERIAL INFECTION

(71) Applicant: TRUSTEES OF DARTMOUTH COLLEGE, Hanover, NH (US)

(72) Inventors: F. Jon Kull, Enfield, NH (US); Ronald K. Taylor, Lebanon, NH (US); Gordon W. Gribble, Lebanon, NH (US); Evans O. Onyango, Hanover, NH (US); Anne R. Kelley, Campton, NH (US)

(73) Assignee: TRUSTEES OF DARTMOUTH COLLEGE, Hanover, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/785,193

(22) Filed: Oct. 16, 2017

(65) Prior Publication Data

US 2018/0029990 A1  Feb. 1, 2018

Related U.S. Application Data

(60) Division of application No. 14/837,139, filed on Aug. 27, 2015, now Pat. No. 9,790,186, which is a continuation-in-part of application No. 13/384,860, filed as application No. PCT/US2010/042704 on Jul. 21, 2010, now abandoned.

(60) Provisional application No. 61/301,264, filed on Feb. 4, 2010, provisional application No. 61/227,190, filed on Jul. 21, 2009.

(51) Int. Cl.
| | |
|---|---|
| C07D 217/12 | (2006.01) |
| C07D 209/12 | (2006.01) |
| C07D 215/14 | (2006.01) |
| A23L 33/10 | (2016.01) |

(52) U.S. Cl.
CPC ............ *C07D 217/12* (2013.01); *A23L 33/10* (2016.08); *C07D 209/12* (2013.01); *C07D 215/14* (2013.01)

(58) Field of Classification Search
CPC ..... A23L 33/10; C07D 209/12; C07D 215/14; C07D 217/12
See application file for complete search history.

(56) References Cited

U.S. PATENT DOCUMENTS

| 3,251,738 | A | 5/1966 | Scherr |
| 5,466,685 | A | 11/1995 | Brown-Skrobot et al. |
| 5,902,578 | A | 5/1999 | Halpin-Dohnalek et al. |
| 6,043,045 | A | 3/2000 | Hoch et al. |
| 7,728,023 | B2 | 6/2010 | Takeuchi et al. |
| 2004/0186292 | A1 | 9/2004 | Wang et al. |
| 2005/0031718 | A1 | 2/2005 | Zhu et al. |
| 2006/0088643 | A1 | 4/2006 | Fugal et al. |
| 2006/0228384 | A1 | 10/2006 | Eldridge |

FOREIGN PATENT DOCUMENTS

| CN | 1478761 | A | 3/2004 |
| EP | 0 737 671 | A2 | 10/1996 |
| WO | 1999/055364 | A2 | 11/1999 |
| WO | 2005/039546 | A2 | 5/2005 |
| WO | 2006/090817 | A1 | 8/2006 |
| WO | 2007/000436 | A1 | 1/2007 |

OTHER PUBLICATIONS

Ribeiro (J of the Chemical Soc. Perkin Transactions 1: Organic and Bio-Organic Chemistry, (1983), (1), 87-91). (Year: 1983).*
Handbook of Pharmaceutical Excipients (p. 168-269, 2005). (Year: 2005).*
Handbook of Pharmaceutical Excipients (2006). (Year: 2006).*
Arizona Department of Health Services (Aug. 2004) "Cholera: Bioterrorism Agent Profiles for Healt Care Workers," 3 pages.
Blomstrand (1960) "Analysis of Human Bile Lipids by Gas-Liquid Chromatography," Acta Chem. Scand. 14(5):1006-1010.
Bridge et al. (1950) "492. The seed fat of Macadamia ternifolia," J. Chem. Soc. 1950:2396-2399.
Chatterjee et al. (2007) "Effect of Fatty Acids and Cholesterol Present in Bile on Expression of Virulence Factors and Motility of Vibrio cholerae," Infection and Immunity. 75(4):1946-1953.
Cheung et al. (2004) "Regulation of virulence determinants in vitro and in vivo in *Staphylococcus aureus*," FEMS Immunol. Med. Microbiol. 40:1-9.
Childers et al. (2011) "N-terminal Residues of the Vibrio cholerae Virulence Regulatory Protein ToxT Involved in Dimerization and Modulation by Fatty Acids," The Journal of Biological Chemistry. 286(32):28644-28655.
Clarke et al. (2007) "The *Staphylococcus aureus* Surface Protein IsdA Mediates Resistance to Innate Defenses of Human Skin," Cell Host & Microbe. 1:199-212.
Echeverria et al. (1985) "A comparative study of enterotoxigenic *Escherichia coil, Shigella, Aeromonas*, and *Vibrio* as etiologies of diarrhea in northeastern Thailand," Am. J. Trop. Med. Hyg. 34(3):547-554.
findmeacure.com (2009) "Sea-Buckthorn" Accessible on the Internet at URL: http://findmeacure.com/2009/05131/sea-buckthorn.
Hung et al. (2005) "Small-Molecule Inhibitor of Vibrio cholerae Virulence and Intestinal Colonization," Science. 310(5748):670-674.
Labandeira-Rey et al. (2007) "*Staphylococcus aureus* Panton-Valentine leukocidin causes necrotizing pneumonia," Science. 315:1130-1133.
Louisiana Office of Public Health and Infectious Disease Epidemiology Section (2013) "Information on *Staphylococcus aureus*," 1 page.

(Continued)

*Primary Examiner* — Umamaheswari Ramachandran
(74) *Attorney, Agent, or Firm* — Lathrop Gage LLP (57) ABSTRACT

Bicyclic compounds for decreasing the expression of bacterial virulence factors thereby preventing, mitigating, or treating bacterial infection are provided.

12 Claims, 2 Drawing Sheets

Specification includes a Sequence Listing.

(56) References Cited

OTHER PUBLICATIONS

Luong et al. (2003) "Mgr, a novel global regulator in *Staphylococcus aureus*," J. Bacteriology. 185(13):3703-3710.
Porter et al. (1998) "Two highly related regulatory proteins, Shigella flexneri VirF and enterotoxigenic *Escherichia coli* Rns, have common and distinct regulatory properties," FEMS Microbiology Letters. 162:303-309.
Schuhmacher et al. (1999) "Environmental Signals Modulate ToxT-Dependent Virulence Factor Expression on Vibrio cholerae," Journal of Bacteriology. 181(5):1508-1514.
Wille et al. (2003) "Palmitoleic Acid Isomer (C16:106) in Human Skin Sebum is Effective against Gram-Positive Bacteria," Skin Pharmacology and Applied Skin Physiology. 16:176-187.
Yang et al. (2001) "Fatty acid composition of lipids in sea buckthorn (*Hippophae rhamnoides* L) berries of different origins," J. Agric. Food Chem. 49:1939-1947.
Zhu et al. (2003) "Quorum sensing-dependent biofilms enhance colonization in Vibrio cholerae," Dev. Cell. 5:647-656.
International Search Report with Written Opinion corresponding to International Patent Application No. PCT/US2010/042704, dated Oct. 20, 2010.
Ballantine et al. (1960) "459. The chemistry of bacteria. Part VIII. The synthesis of violacein and related compounds," J. Chem. Soc. 1960:2292-2299.
Chemical Abstracts [Online] Accession No. 126:7829. Record for EP 0 737 671 A2 (Published 1996), 2 pgs.
Chemical Abstracts [Online] Accession No. 140:303654. Record for US 20040186292 A1 (Published 2004), 1 pg.
Chemical Abstracts [Online] Accession No. 142:113345. Record for CN 1478761 A (Published 2004), 1 pg.
Chemical Abstracts [Online] Accession No. 142:441900. Record for WO 2005/039546 A2 (Published 2005), 2 pgs.
Chemical Abstracts [Online] Accession No. 145:292868. Record for WO 2006/090817 A1 (Published 2006),1 pg.
Chemical Abstracts [Online] Accession No. 146:121844. Record for WO 2007/000436 A1 (Published 2007), 3 pgs.
Chemical Abstracts [Online] Accession No. 148:27358. Record for Geske et al. (2007) J. Am. Chem. Soc. 129(44):13613-13625, 2 pgs.
Chemical Abstracts [Online] Accession No. 54:118162. Record for Ballantine et al. (1960) J. Chem. Soc. 1960:2292-2299, 3 pgs.
Geske et al. (2007) "Modulation of Bacterial Quorum Sensing with Synthetic Ligands: Systematic Evaluation of N-Acylated Homoserine Lactones in Multiple Species and New Insights into Their Mechanisms of Action," J. Am. Chem. Soc. 129(44):13613-13625.
Morshed et al. (2005) "Bacteria Killing Kinetics of the Four Plant Hormones ," Pakistan Journal of Biological Sciences. 8(7):1025-1029.
STN Chemical Catalogue [Online] (Entered Apr. 30, 2008) Registry No. 1018591-54-2, 1 pg.
STN Chemical Catalogue [Online] (Entered Apr. 30, 2008) Registry No. 1018591-62-2, 1 pg.
STN Chemical Catalogue [Online] (Entered Apr. 30, 2008) Registry No. 1018591-66-6, 1 pg.
STN Chemical Catalogue [Online] (Entered Dec. 10, 2008) Registry No. 1082847-53-7, 1 pg.
STN Chemical Catalogue [Online] (Entered Jan. 21, 2009) Registry No. 1094654-43-9, 1 pg.
STN Chemical Catalogue [Online] (Entered Jan. 23, 2008) Registry No. 1000532-59-1, 1 pg.
STN Chemical Catalogue [Online] (Entered Jan. 28, 2009) Registry No. 1096948-84-3, 1 pg.
STN Chemical Catalogue [Online] (Entered May 1, 2008) Registry No. 1018635-87-4, 1 pg.
STN Chemical Catalogue [Online] (Entered Nov. 16, 1984) Registry No. 6342-89-8, 1 pg.
STN Chemical Catalogue [Online] (Entered Nov. 16, 1984) Registry No. 64766-86-5, 1 pg.
STN Chemical Catalogue [Online] (Entered Nov. 16, 1984) Registry No. 70067-71-9, 1 pg.
STN Chemical Catalogue [Online] (Entered Oct. 19, 2003) Registry No. 606492-36-8, 1 pg.
STN Chemical Catalogue [Online] (Entered Oct. 19, 2003) Registry No. 606493-44-1, 1 pg.
International Search Report with Written Opinion corresponding to International Patant Application No. PCT/US2016/048517, dated Dec. 8, 2016, 10 pgs.

* cited by examiner

```
          .....170.......180.......190.......200.......210.......220.......230.......240.......250.......260.......270
VC TOXT   TDDLDAMEKISCLVKSDITRNWRWADICGELRTNRMILKKELESRGVKFRELINSIRISYSISLMKTGEFKIKQIAYQSGFASVSNFSTVFKSTMNVAPSEYLFMLTG
          .....HHHHHHHHHH....LLLLHHHHHHHH..LL.HHHHHHHH..LLLHHHHHHHHHHHHHHHHHH..LLLLHHHHH...LL.....HHHHHH...LLL..H.......
EC FAPR   VAVTFSERIVTLLFSDLTRKWKLSDIAEEMHISEISVRKRLEQECLNFNQLILDVRMNQAAKFIIRSDHQIGMIASLVGYTSVSYFIKTFKEYYGVTPKKFEIGIKEN
          ....HHHHHHHHHH....LLLLHHHHHHHH..LL.HHHHHHHH..LLLHHHHHHHHHHHHHHHHHHH.LLLLHHHHHH...L....HHHHHHHH..LLL.HHH..HHHH.
EC PERA   SSKSIVDRVIKVIELDISKNWKLGDVSSSMFMSDSCLRKQLNKENLTFKKIMLDIKMKHASLFLRTTDKNIDEISCLVGFNSTSYFIKVFKEYYNTTPKKYNGVYSIT
          L..HHHHHHHHHHHH...LLLLHHHHHHHH..LLHHHHHHHHH..LLLHHHHHHHHHHHHHHHHHHH.LLLLHHHHHHHH..LLL..HHHHHHHH..LLL..H........
ST SIRC   IKITTKEKVYNIIISDLTRKWSQAEVAGKLFMSVSSLKRKLAAEEVSFSKIYLDARMNQAIKLLRMGAGNISQVATMCGYDTPSYFIAIFKRHFKITPLSFMRITMNH
          ....HHHHHHHHHHH...LLLLHHHHHHHH..LLHHHHHHHHH..LLLHHHHHHHHHHHHHHHHHHH.LLLLHHHHH....LLL..HHHHHHHH..LLL..H.....LL
ST HILD   AQITLKERVYNIISSSPSRQWKLTDVADHIFMSTSTLKRKLAEEGTSFSDIYLSARMNQAAKLLRIGNHNVNAVALKCGYDSTSYFIQCFKKYFKTTPSTFIKMANH
          ....HHHHHHHHHH....LLLLHHHHHHHH..LL.HHHHHHHH..LLLHHHHHHHHHHHHHHHHHHH.LLLLHHHHHH..LLLL..HHHHHHHH..LLL.......LL
SF VIRF   SSLSFSDQIRKIVEKNIEKRWRLSDISNNLNLSEIAVRKRLESEKLTFQQILLDIRMHHAAKLLLNSQSYINDVSRLIGISSPSYFIRKFNEYYGITPKKFYLYHKKF
          ....HHHHHHHHHH.....LLLHHHHHHHH.LLL.HHHHHHHH..LLLHHHHHHHHHHHHHHHHHH..LLL.HHHHHHH..LLL..HHHHHHHH..LLL.HHH......L
YE VIRF   LGNRPEERLQKFMEENYLQGWKLSKFAREFGMGLTTFKELFGTVYGISPRAWISERRILYAHQLLLNGKMSIVDIAMEAGFSSQSYFTQSYRRRFGCTPSQARLTKIA
          ....HHHHHHHHHHH...LLLLHHHHHHHH.LLLHHHHHHHHHH..LLLHHHHHHHHHHHHHHHHHH..LLLLHHHHH...LLLL...HHHHHHHH.LLL..H.......
EC RNS    SVSFFSDKVRNLIEKDLSRKWTLGIIADAFNASEITIRKRLESENTNFNQILMQLRMSKAALLLLENSYQISQISNMIGISSASYFIRIFNKHYGVTPKQFFTYFKGG
          ...HHHHHHHHHHHH...LLLLHHHHHHHH..LL.HHHHHHHH..LLLHHHHHHHHHHHHHHHHHHH.LLLLHHHHHH...LLL..HHHHHHHH..LLL.HH......LL
YP ARAC   SQTLFESIREYIERNYSEPLTRESVAHVFHISPNYLSHLFRNAGNIGFNESVNSARLENAKILLKFYEMKIKEVANVCGFIDSNYFCRLFRKETELTPSEYRQQYRS
          .HHHHHHHHHHHHH.......HHHHHHHH...HHHHHHHHHHHH...HHHHHHHHHHHHHHHHHHH....HHHHHHHHH....HHHHHHHHHHHH...HHHHHHHHH.
BAN ARAC  SHTLFERISSYVHKYYYKDITIHTLTEQNNVNRNRLSYVFRKHAGMGPAEYLLNYRIKMAQKMLCTSGVPVQQIAQAVGIADPFYFSRVFKKRVGISPTKYREKFINN
          .HHHHHHHHHHHHH.......HHHHHHHH...HHHHHHHHHHHHH..HHHHHHHHHHHHHHHHH.......HHHHHHHH....HHHHHHHHHHHH...HHHHHHHHH..
BAB ARAC  SANRQDCERIREFIMANLDRDLTIDLIAQKVAISASTVQRRFKKHYGTTLYNFIKQQRLEAACVALSRDSIPISQAAHLAGYNNTSTFTSAFRKLYGFSPKKMRALGK
          ...HHHHHHHHHHHH.......HHHHHHHH...HHHHHHHHHHHH..HHHHHHHHHHHHHHHHHHHH.....HHHHHHHH....HHHHHHHHHHHH...HHHHHHHH.
CB ARAC   SGDDRVLFKQVSDYIHEYYMDTLTIRSLAELHGVNENRLFYVFSKYAGMGAGDYLMIHRLNRAKELLVTGNAPVVAVAKSVGYHDPYHFSKRFKKQFGISPSKFRDKF
          ...HHHHHHHHHHHHHH.......HHHHHHHH...HHHHHHHHHHH.....HHHHHHHHHHHHHHHH.......HHHHHHHH....HHHHHHHHHHHH...HHHHHHHH
```

FIG. 2

SEQUENCE LISTING

<160> NUMBER OF SEQ ID NOS: 12

<210> SEQ ID NO 1
<211> LENGTH: 108
<212> TYPE: PRT
<213> ORGANISM: Vibrio cholerae

<400> SEQUENCE: 1

Thr Asp Asp Leu Asp Ala Met Glu Lys Ile Ser Cys Leu Val Lys Ser
1               5                   10                  15

Asp Ile Thr Arg Asn Trp Arg Trp Ala Asp Ile Cys Gly Glu Leu Arg
            20                  25                  30

Thr Asn Arg Met Ile Leu Lys Lys Glu Leu Glu Ser Arg Gly Val Lys
        35                  40                  45

Phe Arg Glu Leu Ile Asn Ser Ile Arg Ile Ser Tyr Ser Ile Ser Leu
    50                  55                  60

Met Lys Thr Gly Glu Phe Lys Ile Lys Gln Ile Ala Tyr Gln Ser Gly
65                  70                  75                  80

Phe Ala Ser Val Ser Asn Phe Ser Thr Val Phe Lys Ser Thr Met Asn
                85                  90                  95

Val Ala Pro Ser Glu Tyr Leu Phe Met Leu Thr Gly
            100                 105

<210> SEQ ID NO 2
<211> LENGTH: 108
<212> TYPE: PRT
<213> ORGANISM: Escherichia coli

<400> SEQUENCE: 2

Val Ala Val Thr Phe Ser Glu Arg Ile Val Thr Leu Leu Phe Ser Asp
1               5                   10                  15

Leu Thr Arg Lys Trp Lys Leu Ser Asp Ile Ala Glu Glu Met His Ile
            20                  25                  30

Ser Glu Ile Ser Val Arg Lys Arg Leu Glu Gln Glu Cys Leu Asn Phe
        35                  40                  45

Asn Gln Leu Ile Leu Asp Val Arg Met Asn Gln Ala Ala Lys Phe Ile
    50                  55                  60

Ile Arg Ser Asp His Gln Ile Gly Met Ile Ala Ser Leu Val Gly Tyr
65                  70                  75                  80

Thr Ser Val Ser Tyr Phe Ile Lys Thr Phe Lys Glu Tyr Tyr Gly Val
                85                  90                  95

Thr Pro Lys Lys Phe Glu Ile Gly Ile Lys Glu Asn
            100                 105

<210> SEQ ID NO 3
<211> LENGTH: 108
<212> TYPE: PRT
<213> ORGANISM: Escherichia coli

<400> SEQUENCE: 3

Ser Ser Lys Ser Ile Val Asp Arg Val Ile Lys Val Ile Glu Leu Asp
1               5                   10                  15

Ile Ser Lys Asn Trp Lys Leu Gly Asp Val Ser Ser Ser Met Phe Met
            20                  25                  30

Ser Asp Ser Cys Leu Arg Lys Gln Leu Asn Lys Glu Asn Leu Thr Phe
        35                  40                  45

Lys Lys Ile Met Leu Asp Ile Lys Met Lys His Ala Ser Leu Phe Leu
    50                  55                  60

```
Arg Thr Thr Asp Lys Asn Ile Asp Glu Ile Ser Cys Leu Val Gly Phe
 65                  70                  75                  80

Asn Ser Thr Ser Tyr Phe Ile Lys Val Phe Lys Glu Tyr Tyr Asn Thr
                 85                  90                  95

Thr Pro Lys Lys Tyr Asn Gly Val Tyr Ser Ile Thr
            100                 105
```

<210> SEQ ID NO 4
<211> LENGTH: 107
<212> TYPE: PRT
<213> ORGANISM: Salmonella typhi

<400> SEQUENCE: 4

```
Ile Lys Ile Thr Thr Lys Glu Lys Val Tyr Asn Ile Ile Ser Asp
  1               5                  10                  15

Leu Thr Arg Lys Trp Ser Gln Ala Glu Val Ala Gly Lys Leu Phe Met
                 20                  25                  30

Ser Val Ser Ser Leu Lys Arg Lys Leu Ala Ala Glu Glu Val Ser Phe
             35                  40                  45

Ser Lys Ile Tyr Leu Asp Ala Arg Met Asn Gln Ala Ile Lys Leu Leu
         50                  55                  60

Arg Met Gly Ala Gly Asn Ile Ser Gln Val Ala Thr Met Cys Gly Tyr
 65                  70                  75                  80

Asp Thr Pro Ser Tyr Phe Ile Ala Ile Phe Lys Arg His Phe Lys Ile
                 85                  90                  95

Thr Pro Leu Ser Phe Met Arg Thr Met Asn His
            100                 105
```

<210> SEQ ID NO 5
<211> LENGTH: 107
<212> TYPE: PRT
<213> ORGANISM: Salmonella typhimurium

<400> SEQUENCE: 5

```
Ala Gln Ile Thr Leu Lys Glu Arg Val Tyr Asn Ile Ile Ser Ser Ser
  1               5                  10                  15

Pro Ser Arg Gln Trp Lys Leu Thr Asp Val Ala Asp His Ile Phe Met
                 20                  25                  30

Ser Thr Ser Thr Leu Lys Arg Lys Leu Ala Glu Glu Gly Thr Ser Phe
             35                  40                  45

Ser Asp Ile Tyr Leu Ser Ala Arg Met Asn Gln Ala Ala Lys Leu Leu
         50                  55                  60

Arg Ile Gly Asn His Asn Val Asn Ala Val Ala Leu Lys Cys Gly Tyr
 65                  70                  75                  80

Asp Ser Ser Tyr Phe Ile Gln Cys Phe Lys Lys Tyr Phe Lys Thr
                 85                  90                  95

Thr Pro Ser Thr Phe Ile Lys Met Ala Asn His
            100                 105
```

<210> SEQ ID NO 6
<211> LENGTH: 108
<212> TYPE: PRT
<213> ORGANISM: Shigella flexneri

<400> SEQUENCE: 6

```
Ser Ser Leu Ser Phe Ser Asp Gln Ile Arg Lys Ile Val Glu Lys Asn
  1               5                  10                  15
```

Ile Glu Lys Arg Trp Arg Leu Ser Asp Ile Ser Asn Asn Leu Asn Leu
            20                  25                  30

Ser Glu Ile Ala Val Arg Lys Arg Leu Glu Ser Glu Lys Leu Thr Phe
        35                  40                  45

Gln Gln Ile Leu Leu Asp Ile Arg Met His His Ala Ala Lys Leu Leu
    50                  55                  60

Leu Asn Ser Gln Ser Tyr Ile Asn Asp Val Ser Arg Leu Ile Gly Ile
65                  70                  75                  80

Ser Ser Pro Ser Tyr Phe Ile Arg Lys Phe Asn Glu Tyr Tyr Gly Ile
                85                  90                  95

Thr Pro Lys Lys Phe Tyr Leu Tyr His Lys Lys Phe
            100                 105

<210> SEQ ID NO 7
<211> LENGTH: 108
<212> TYPE: PRT
<213> ORGANISM: Yersinia enterocolitica

<400> SEQUENCE: 7

Leu Gly Asn Arg Pro Glu Glu Arg Leu Gln Lys Phe Met Glu Glu Asn
1               5                   10                  15

Tyr Leu Gln Gly Trp Lys Leu Ser Lys Phe Ala Arg Glu Phe Gly Met
            20                  25                  30

Gly Leu Thr Thr Phe Lys Glu Leu Phe Gly Thr Val Tyr Gly Ile Ser
        35                  40                  45

Pro Arg Ala Trp Ile Ser Glu Arg Arg Ile Leu Tyr Ala His Gln Leu
    50                  55                  60

Leu Leu Asn Gly Lys Met Ser Ile Val Asp Ile Ala Met Glu Ala Gly
65                  70                  75                  80

Phe Ser Ser Gln Ser Tyr Phe Thr Gln Ser Tyr Arg Arg Arg Phe Gly
                85                  90                  95

Cys Thr Pro Ser Gln Ala Arg Leu Thr Lys Ile Ala
            100                 105

<210> SEQ ID NO 8
<211> LENGTH: 108
<212> TYPE: PRT
<213> ORGANISM: Escherichia coli

<400> SEQUENCE: 8

Ser Val Ser Phe Phe Ser Asp Lys Val Arg Asn Leu Ile Glu Lys Asp
1               5                   10                  15

Leu Ser Arg Lys Trp Thr Leu Gly Ile Ile Ala Asp Ala Phe Asn Ala
            20                  25                  30

Ser Glu Ile Thr Ile Arg Lys Arg Leu Glu Ser Glu Asn Thr Asn Phe
        35                  40                  45

Asn Gln Ile Leu Met Gln Leu Arg Met Ser Lys Ala Ala Leu Leu Leu
    50                  55                  60

Leu Glu Asn Ser Tyr Gln Ile Ser Gln Ile Ser Asn Met Ile Gly Ile
65                  70                  75                  80

Ser Ser Ala Ser Tyr Phe Ile Arg Ile Phe Asn Lys His Tyr Gly Val
                85                  90                  95

Thr Pro Lys Gln Phe Phe Thr Tyr Phe Lys Gly Gly
            100                 105

<210> SEQ ID NO 9
<211> LENGTH: 107

<212> TYPE: PRT
<213> ORGANISM: Yersinia pestis

<400> SEQUENCE: 9

Ser Gln Thr Leu Phe Glu Ser Ile Arg Glu Tyr Ile Glu Arg Asn Tyr
1               5                   10                  15

Ser Glu Pro Leu Thr Arg Glu Ser Val Ala His Val Phe His Ile Ser
            20                  25                  30

Pro Asn Tyr Leu Ser His Leu Phe Arg Asn Ala Gly Asn Ile Gly Phe
        35                  40                  45

Asn Glu Ser Val Asn Ser Ala Arg Leu Glu Asn Ala Lys Ile Leu Leu
50                  55                  60

Lys Phe Tyr Glu Met Lys Ile Lys Glu Val Ala Asn Val Cys Gly Phe
65                  70                  75                  80

Ile Asp Ser Asn Tyr Phe Cys Arg Leu Phe Arg Lys Glu Thr Glu Leu
                85                  90                  95

Thr Pro Ser Glu Tyr Arg Gln Gln Tyr Arg Ser
            100                 105

<210> SEQ ID NO 10
<211> LENGTH: 108
<212> TYPE: PRT
<213> ORGANISM: Bacillus anthracis

<400> SEQUENCE: 10

Ser His Thr Leu Phe Glu Arg Ile Ser Ser Tyr Val His Lys Tyr Tyr
1               5                   10                  15

Tyr Lys Asp Ile Thr Ile His Thr Leu Thr Glu Gln Asn Asn Val Asn
            20                  25                  30

Arg Asn Arg Leu Ser Tyr Val Phe Arg Lys His Ala Gly Met Gly Pro
        35                  40                  45

Ala Glu Tyr Leu Leu Asn Tyr Arg Ile Lys Met Ala Gln Lys Met Leu
50                  55                  60

Cys Thr Ser Gly Val Pro Val Gln Gln Ile Ala Gln Ala Val Gly Ile
65                  70                  75                  80

Ala Asp Pro Phe Tyr Phe Ser Arg Val Phe Lys Lys Arg Val Gly Ile
                85                  90                  95

Ser Pro Thr Lys Tyr Arg Glu Lys Phe Ile Asn Asn
            100                 105

<210> SEQ ID NO 11
<211> LENGTH: 108
<212> TYPE: PRT
<213> ORGANISM: Brucella abortus

<400> SEQUENCE: 11

Ser Ala Asn Arg Gln Asp Cys Glu Arg Ile Arg Glu Phe Ile Met Ala
1               5                   10                  15

Asn Leu Asp Arg Asp Leu Thr Ile Asp Leu Ile Ala Gln Lys Val Ala
            20                  25                  30

Ile Ser Ala Ser Thr Val Gln Arg Arg Phe Lys Lys His Tyr Gly Thr
        35                  40                  45

Thr Leu Tyr Asn Phe Ile Lys Gln Gln Arg Leu Glu Ala Ala Cys Val
50                  55                  60

Ala Leu Ser Arg Asp Ser Ile Pro Ile Ser Gln Ala Ala His Leu Ala
65                  70                  75                  80

Gly Tyr Asn Asn Thr Ser Thr Phe Thr Ser Ala Phe Arg Lys Leu Tyr

```
                        85                  90                  95
Gly Phe Ser Pro Lys Lys Met Arg Ala Leu Gly Lys
                100                 105

<210> SEQ ID NO 12
<211> LENGTH: 108
<212> TYPE: PRT
<213> ORGANISM: Clostridium botulinum

<400> SEQUENCE: 12

Ser Gly Asp Asp Arg Val Leu Phe Lys Gln Val Ser Asp Tyr Ile His
1               5                   10                  15
Glu Tyr Tyr Met Asp Thr Leu Thr Ile Arg Ser Leu Ala Glu Leu His
                20                  25                  30
Gly Val Asn Glu Asn Arg Leu Phe Tyr Val Phe Ser Lys Tyr Ala Gly
            35                  40                  45
Met Gly Ala Gly Asp Tyr Leu Met Ile His Arg Leu Asn Arg Ala Lys
        50                  55                  60
Glu Leu Leu Val Thr Gly Asn Ala Pro Val Val Ala Val Ala Lys Ser
65                  70                  75                  80
Val Gly Tyr His Asp Pro Tyr His Phe Ser Lys Arg Phe Lys Lys Gln
                85                  90                  95
Phe Gly Ile Ser Pro Ser Lys Phe Arg Asp Lys Phe
                100                 105
```

COMPOSITION AND METHOD FOR PREVENTION, MITIGATION OR TREATMENT OF AN ENTEROPATHOGENIC BACTERIAL INFECTION

CROSS-REFERENCE TO RELATED APPLICATIONS

This application is a divisional application of U.S. patent application Ser. No. 14/837,139 filed Aug. 27, 2015, which is a continuation-in-part application of U.S. patent application Ser. No. 13/384,860 filed Feb. 23, 2012, which is a 35 U.S.C. § 371 filing of International Application No. PCT/US2010/042704 filed Jul. 21, 2010, which claims the benefit of priority to U.S. Provisional Application Ser. No. 61/301,264 filed Feb. 4, 2010 and U.S. Provisional Application Ser. No. 61/227,190 filed Jul. 21, 2009, the contents of which are incorporated herein by reference in their entireties.

GOVERNMENT SUPPORT

This invention was made with government support under contract numbers AI072661 and AI039654 awarded by the National Institutes of Health. The government has certain rights in the invention.

BACKGROUND

The increasing resistance of bacterial pathogens to antibiotics, combined with fundamental advances in understanding the mechanisms and regulation of bacterial virulence, has prompted the identification of pathogen anti-virulence drugs that antagonize the activity of virulence factors. Cholera is an acute intestinal infection caused by the bacterium *Vibrio cholerae*, a gram-negative flagellated bacillus. In addition to being a class B bioterrorism threat, cholera is more widespread today than it was in the previous century. The expression of *V. cholerae*'s primary virulence factors, the toxin-coregulated pilus (TCP) and cholera toxin (CT), occurs via a transcriptional cascade involving several activator proteins, and serves as a paradigm for the regulation of bacterial virulence. Strains of *V. cholerae* capable of causing the significant epidemics and pandemics of cholera that have occurred throughout history possess two genetic elements, the *Vibrio* pathogenicity island (VPI) and the lysogenic CTX phage. Both of these elements have inserted into the circular chromosome I and are present in the pathogenic forms of the organism. The VPI contains the genes responsible for the synthesis and assembly of the essential colonization factor TCP, and the CTX phage encodes the CT genes. Expression of the TCP and CT genes is coordinately regulated at the transcriptional level by a virulence cascade involving activator proteins encoded both within the VPI and the ancestral genome. AphA and AphB initiate the expression of the cascade by a novel interaction at the tcpPH promoter. AphA is a member of a new regulator family and AphB is a LysR-type activator, one of the largest transcriptional regulatory families. Once expressed, cooperation between TcpP/TcpH and the homologous transmembrane activators ToxR/ToxS activates the toxT promoter. ToxT, an AraC/XylS (A/X) type regulator, then directly activates the promoters of the primary virulence factors. Thus, ToxT is the paramount regulator of virulence gene expression.

ToxT inhibitors have been identified and shown to provide protection against intestinal colonization by *V. cholerae*. For example, bile (Schuhmacher, et al. (1999) *J. Bacteriol.* 181:1508-14) and several of its unsaturated fatty acid constituents, i.e., oleic acid, linoleic acid, and arachidonic acid (Chatterjee, et al. (2007) *Infect. Immun.* 75:1946-53) have been shown to inhibit virulence factor gene expression. Similarly, virstatin, a small molecule 4-[N-(1,8-naphthalimide)]-n-butyric acid, has been shown to inhibit virulence regulation in *V. cholerae* (Hung, et al. (2005) *Science* 310(5748):670-4). Further, U.S. Pat. No. 5,866,150 teaches compounds having the structure: $CH_3(CH_2)_n$—$CH$=$CH$—$CH_2CH$=$CH$—$(CH_2)$—$R$—$COOR'$ for use in treating bacterial infections including, e.g., *S. aureus, V. cholera, S. dysenteria, B. substilis,* and *S. typhemurium*.

High resolution structure of ToxT has shown that ToxT contains an almost completely buried and solvent inaccessible sixteen carbon fatty acid bound to a pocket in the N-terminal domain, which can influence its DNA binding activity. In particular, virulence gene expression can be reduced between 6-8 fold with cis-palmitoleic acid and 10-15 fold with oleic acid (Lowden, et al. (2010) *Proc. Natl. Acad. Sci. USA* 107:2860-5).

SUMMARY OF THE INVENTION

This invention provides a compound having the structure of Formula I, or hydrates, isomers, prodrugs or pharmaceutically acceptable salts of Formula I:

Formula I wherein $R^1$ is hydrogen or polar group; $R^2$ is hydrogen, alkenyl, or oxo; X is —CHCH—, —NH—, —C=N—, —N=C—, —C—NH— or —NH—C—; n is 0-6; and dashed lines represent bonds that are independently present or absent. A pharmaceutical, nutraceutical, nutritional, medical nutrition food or functional food composition containing a compound of Formula I is also provided.

This invention also includes methods for decreasing expression of a bacterial virulence factor and preventing, mitigating, or treating an infection by a bacterium that expresses an A/X regulatory protein using a compound of Formula I. In some embodiments the pathogenic bacterium is *Vibrio cholerae, Escherichia coli, Shigella flexneri, Yersinia enterocolitica, Yersinia pestis, Brucella abortus Salmonella typhi, Bacillus anthracis, Clostridium botulinum, Listeria monocytogenes, Staphylococcus aureus* or *Salmonella typhimurium*.

BRIEF DESCRIPTION OF THE DRAWINGS

FIG. 2 shows the effects of compound 1 on tcp expression. V. cholerae cells were grown in LB pH 6.5 at 30° C. for 18 hours±the indicated inhibitor in methanol. β-galactosidase activity of a tcp-lacZ reporter construct was determined. β-galactosidase units are shown for a wild-type strain treated with methanol (MeOH), 0.01% oleic acid (0.01% OA), 0.02% oleic acid (0.02% OA), or 0.02% compound 1 (Comp1) as compared to an untreated control (ToxT) and an untreated ToxT deletion strain (ΔToxT).

DETAILED DESCRIPTION OF THE INVENTION

A class of bicyclic compounds has now been identified, which exhibits anti-virulence activity against V. cholerae. The compounds of this invention were designed to bind to the pocket located in the N-terminus of ToxT (Lowden, et al. (2010) Proc. Natl. Acad. Sci. USA 107:2860-5), thereby disrupting DNA binding activity and virulence gene expression. Given that ToxT homologues are found in a wide variety bacterial pathogens, the compounds of this invention find use as broad spectrum anti-virulence agents in the treatment of antibiotic-resistant bacterial infections as well as in prophylactic treatment of infections, e.g., for travelers or military personnel in areas with suboptimal water and/or food quality. Moreover, because the compounds of this invention are highly specific for pathogens, the normal bacterial flora of the gut is not affected.

Compounds of this invention have the structure of Formula I, which includes hydrates, isomers, prodrugs or pharmaceutically acceptable salts of Formula I:

Formula I wherein $R^1$ is hydrogen (H) or polar group, e.g., a $C_1$-$C_6$ alkyl, $C_1$-$C_6$ alkenyl, $C_4$-$C_6$ aryl, halo (e.g., F, Cl, or Br) $CF_3$, $OCH_3$, $NO_2$, CN, OH, $NMe_2$, COOH, or $COOCH_3$; $R^2$ is hydrogen (H), alkenyl (=$CH_2$), or oxo (=O); X is —CHCH—, —NH—, —C=N—, —N=C—, —C—NH— or —NH—C—; n is 0-6; and dashed lines represent bonds that are independently present or absent. In certain embodiments, n is 3, 4, or 5.

In some embodiments, the invention is a compound having the structure of Formula II, which includes hydrates, isomers, prodrugs or pharmaceutically acceptable salts of Formula II:

Formula II wherein $R^1$ is a polar group, e.g., a $C_1$-$C_6$ alkyl, a $C_1$-$C_6$ alkenyl, $C_4$-$C_6$ aryl, halo, $CF_3$, $OCH_3$, $NO_2$, CN, OH, $NMe_2$, COOH, or $COOCH_3$; X is —CH—, —NH—, —C=N—, —N=C—, —C—NH— or —NH—C—; $R^2$ is hydrogen (H), alkenyl (=$CH_2$), or oxo (=O); and dashed lines represent bonds that are independently present or absent.

As used herein, the term "alkyl" refers to a straight or branched chain hydrocarbon, preferably having from one to six carbon atoms (i.e., $C_1$-$C_6$). Examples of "alkyl" as used herein include methyl, ethyl, propyl, isopropyl, n-butyl, isopentyl, n-pentyl, and the like, as well as substituted versions thereof. In particular embodiments, an alkyl of the invention is a $C_1$-$C_3$ alkyl.

The term "alkenyl" refers to a straight or branched chain aliphatic hydrocarbon containing one or more carbon-to-carbon double bonds that may be optionally substituted, with multiple degrees of substitution included within the present invention. Examples include, but are not limited to, vinyl, allyl, and the like, as well as substituted versions thereof.

The term "aryl" refers to a monovalent group with an aromatic carbon atom as the point of attachment, said carbon atom forming part of a four-, five- or six-membered aromatic ring structure wherein the ring atoms are all carbon, and wherein the monovalent group is composed of carbon and hydrogen. Non-limiting examples of aryl groups include phenyl, methylphenyl, (dimethyl)phenyl, -ethylphenyl, propylphenyl, —$C_6H_4CH(CH_3)_2$, —$C_6H_4CH(CH_2)_2$, methylethylphenyl, vinylphenyl, naphthyl, and the monovalent group derived from biphenyl. In particular embodiments, the aryl is a phenyl group.

Any undefined valency on an atom of a structure shown in this application implicitly represents a hydrogen atom bonded to the atom.

Exemplary compounds of the invention include, but are not limited to:

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

An "isomer" of a first compound is a separate compound in which each molecule contains the same constituent atoms as the first compound, but where the configuration of those atoms in three dimensions differs.

"Pharmaceutically acceptable salts" means salts of compounds of the present invention which are pharmaceutically acceptable, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and di-carboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiary-butylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

Compounds of the invention may also exist in prodrug form. Since prodrugs are known to enhance numerous desirable qualities of pharmaceuticals, e.g., solubility, bioavailability, manufacturing, etc., the compounds employed in some methods of the invention may, if desired, be delivered in prodrug form. Thus, the invention contemplates prodrugs of compounds of the present invention as well as methods of delivering prodrugs. Prodrugs of the compounds employed in the invention may be prepared by modifying functional groups present in the compound in such a way that the modifications are cleaved, either in routine manipulation or in vivo, to the parent compound. Accordingly, prodrugs include, for example, compounds described herein in which a hydroxy or carboxy group is bonded to any group that, when the prodrug is administered to a patient, cleaves to form a hydroxy or carboxylic acid, respectively. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, gentisates, isethionates, di-p-toluoyltartrates, methanesulfonates, ethanesulfonates, benzenesulfonates, p-toluenesulfonates, cyclohexylsulfamates, quinates, esters of amino acids, and the like.

Compounds of the invention can be prepared as described herein (see Example 1) or using any suitable methodology routinely practiced in the art, and be analyzed for their pharmacological properties by routine methodologies. For example, kinetic solubility can be measured using a direct UV absorbance method or thermodynamic solubility can be measured. In addition, stability in gastrointestinal fluids can be determined by conventional methods (Asafu-Adjaye, et al. (2007) *J. Pharm. Biomed. Anal.* 43:1854-1859), e.g., 1 hour in simulated gastric fluid (pH 1.2, pepsin) at 37° C. and/or 3 hours in simulated intestinal fluid (pH 6.8, pancreatin). Furthermore, using the Parallel Artificial Membrane Permeability Assay (PAMPA)-blood-brain barrier (BBB) permeability assay (Di, et al. (2009) *J. Pharm. Sci.* 98:1980-1991) or B-P dialysis (Kalvass & Maurer (2002) *Biopharm. Drug Dispos.* 23(8):327-38), brain penetration can be assessed. Furthermore, lipophilicity can be estimated by partitioning between octanol and water using a shake flask method or pH metric method and permeability can be assessed using the Caco-2 cell layer method of PAMPA assay.

A compound of this invention may be administered in a pharmaceutical composition by various routes including, but not limited to, intradermal, intramuscular, intraperitoneal (e.g., by injection), intravenous, subcutaneous, intranasal, epidural, oral, sublingual, intracerebral, transdermal, rectal, or topical administration. Depending on the route of administration, the active compound may be coated. For example, to administer the therapeutic compound by a route other than parenteral administration, it may be necessary to coat the compound with, or co-administer the compound with, a material to prevent its inactivation. By way of illustration, the therapeutic compound may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan, et al. (1984) *J. Neuroimmunol.* 7:27).

When the compound is to be administered parenterally, intraperitoneally, intraspinally, or intracerebrally, dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filtered sterilization. Generally, dispersions are prepared by incorporating the therapeutic compound into a sterile carrier which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., the therapeutic compound) plus any additional desired ingredient from a previously sterile-filtered solution thereof.

The compound can be orally administered, for example, with an inert diluent or an assimilable edible carrier. The therapeutic compound and other ingredients may also be enclosed in a hard or soft shell gelatin capsule, compressed into tablets, or incorporated directly into the subject's diet. For oral therapeutic administration, the therapeutic compound may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical carrier. The specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of a selected condition in a subject.

In addition to conventional pharmaceutical compositions, this invention also provides nutraceuticals; nutritional compositions, such as dietary supplements; medical nutrition or functional foods including a compound of Formula I. Such compositions can be prepared by mixing one or more compounds of the invention with an edible nutritionally acceptable solid or liquid carriers and/or excipients, e.g., fillers, such as cellulose, lactose, sucrose, mannitol, sorbitol, and calcium phosphates; and binders, such as starch, gelatin, tragacanth, methylcellulose and/or polyvinylpyrrolidone (PVP). Optional additives include lubricants and flow conditioners, e.g., silicic acid, silicon dioxide, talc, stearic acid, magnesium/calcium stearates and polyethylene glycol (PEG) diluents; disintegrating agents, e.g., starch, carboxymethyl starch, cross-linked PVP, agar, alginic acid and alginates, coloring agents, flavoring agents and melting agents. The composition of the invention can optionally include conventional food additives, such as emulsifiers, stabilizers, sweeteners, preservatives, chelating agents, osmotic agents, buffers or agents for pH adjustment, acidulants, thickeners, texturizers and the like.

In addition to the above, the compositions of the present invention can further include antibiotics (e.g., tetracyclines), probiotics, prebiotics, anti-LPS sIgA (Apter, et al. (1993) *Infect. Immun.* 61(12):5279-5285), as well as other monounsaturated fatty acids such as oleic acid or palmitoleic acid to facilitate the prevention, mitigation and/or treatment of a bacterial infection. As such, compositions containing other monounsaturated fatty acids such as oleic acid, palmitoleic acid and vaccenic acid and their use in the treatment of bacterial infections are also embraced by the present invention.

Suitable product formulations according to the present invention include sachets, soft gel, powders, syrups, pills, capsules, tablets, liquid drops, sublinguals, patches, suppositories, liquids, injectables and the like. Also contemplated are food and beverage products containing one or more compounds of the present invention, such as solid food products, like bars (e.g., nutritional bars or cereal bars), powdered drinks, dairy products, breakfast cereals, muesli, candies, confectioneries, cookies, biscuits, crackers, chocolate, chewing-gum, desserts and the like; liquid comestibles, like soft drinks, juice, sports drinks, milk drinks, milkshakes, yogurt drinks or soups, etc. The addition of one or more compounds of the invention to animal feed is also included within the scope of this invention.

The compositions of the invention can be provided as a component of a meal, e.g., a nutritional or dietary supplement, in the form of a health drink, a snack or a nutritionally fortified beverage, as well as a conventional pharmaceutical, e.g., a pill, a tablet or a softgel, for example.

Figure 1:
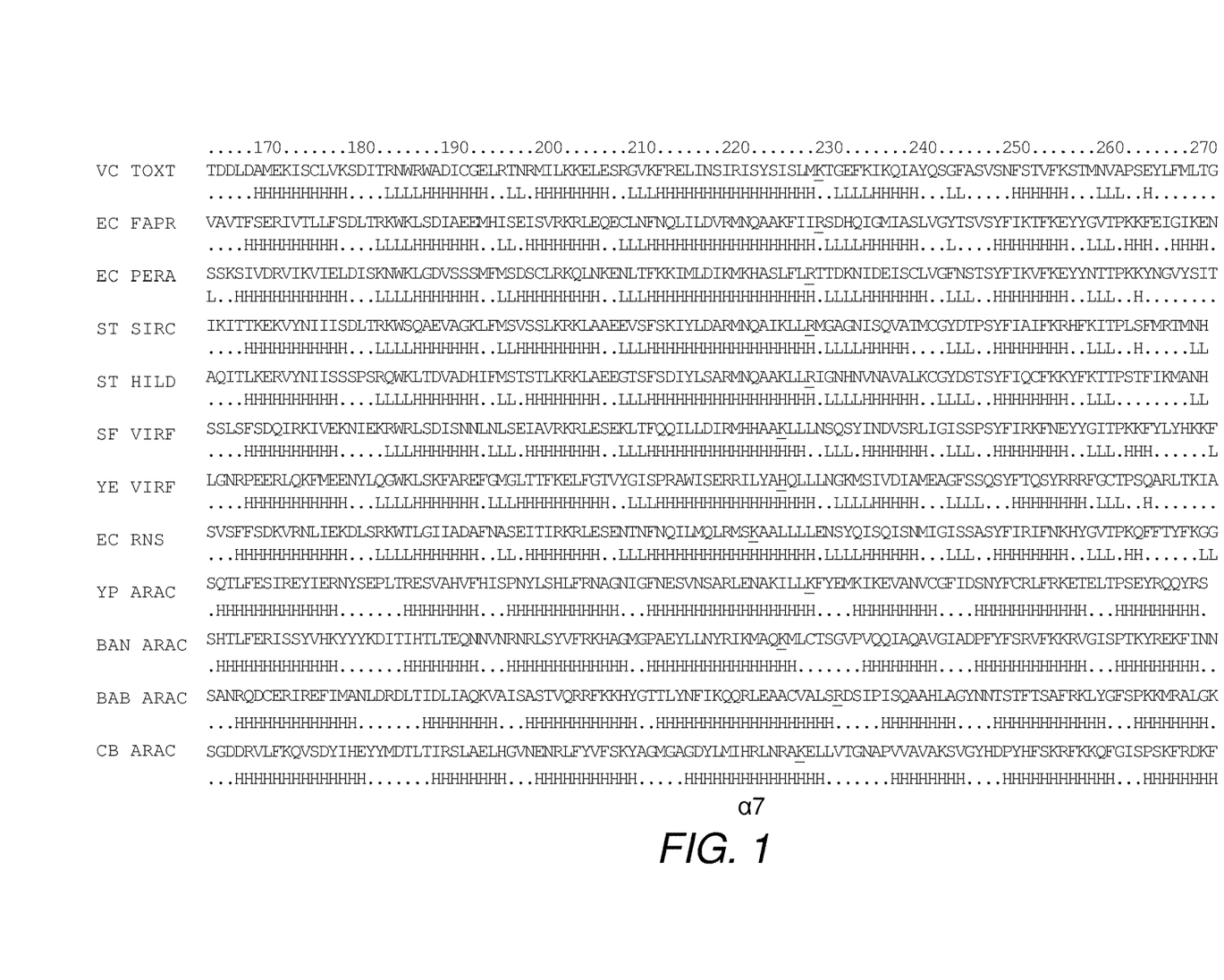
FIG. 1 shows a sequence alignment of A/X family members from *V. cholerae* (Vc ToxT; SEQ ID NO:1), an *E. coli* ETEC strain (Ec FapR; SEQ ID NO:2), an *E. coli* EPEC strain (Ec PerA; SEQ ID NO:3), *S. typhi* (St SirC; SEQ ID NO:4), *S. typhimurium* (St HilD; SEQ ID NO:5), *S. flexneri* (Sf VirF; SEQ ID NO:6), *Y. enterocolitica* (Ye VirF; SEQ ID NO:7), an *E. coli* ETEC strain (Ec Rns; SEQ ID NO:8), *Y. pestis* (Yp AraC; SEQ ID NO:9), *B. anthracis* (Ban AraC; SEQ ID NO:10), *B. abortus* (Bab AraC; SEQ ID NO:11) and C. botulinum (Cb AraC; SEQ ID NO:12). Secondary structure predictions and homology modeling indicate common helix (H), loop/turn (L) and lysines or other positive amino acids (underlined residues) at positions homologous to those identified in ToxT. The entire sequence lengths were compared, but only partial sequences are shown here.

ToxT belongs to the AraC/XylS (A/X) superfamily of regulatory proteins. This family is composed of approximately 1,974 members identified in 149 bacterial genomes including *Bacillus anthracis, Listeria monocytogenesi* and *Staphylococcus aureus* (Ibarra, et al. (2008) *Genetica* 133: 65-76), and is known for its role in virulence gene regulation. The crystal structure of ToxT identified a binding pocket enclosed by residues Y12, Y20, F22, L25, I27, K31, F33, L61, F69, L71, V81, and V83 from the N-terminal domain and residues I226, K230, M259, V261, Y266, and M269 from the C-terminal domain. The volume of this predominantly hydrophobic pocket is 780.9 Å$^3$ as calculated by the program CASTp. This pocket contains a sixteen-carbon fatty acid with a negatively charged carboxylate head group forming salt bridges with both K31 from the N-terminal domain and K230 from the C-terminal domain. Using secondary structure prediction and homology modeling, multiple candidates from the A/X protein superfamily were identified, which contained lysines or other positive amino acids at positions homologous to those identified in ToxT. This analysis indicated that A/X regulatory proteins from many pathogenic bacteria, including *Vibrio cholerae, Escherichia coli, Shigella flexneri, Yersinia enterocolitica, Yersinia pestis, Brucella abortus, Salmonella typhi, Bacillus anthracis,* and *Clostridium botulinum* (FIG. 1), as well as *Staphylococcus aureus* and *Salmonella typhimurium* contain with homologous lysine residues and/or homologous ligand binding pockets. Thus, use of compositions herein can be broadly applied to treat enteric bacterial infections that cause travelers' diarrhea, *salmonella*, brucellosis, botulism, dysentery, and typhoid fever, diseases infecting some 4 billion people annually worldwide.

Thus, the present invention embraces compositions containing one or more compounds of the invention for use in methods for decreasing or inhibiting the expression of bacterial virulence genes. This method is carried out by contacting a pathogenic bacterium with a composition of the present invention so that the expression of at least one virulence factor, e.g., TCP and/or CT in *V. cholerae*, is measurably decreased as compared to bacteria not contacted with the composition of the invention. A decrease or inhibition of virulence factor expression can be measured using any conventional method for monitoring nucleic acid or protein levels in a cell, e.g., northern blot analysis, RT-PCR analysis, dot blot analysis, western blot analysis and the like. Desirably, the composition of the invention decreases virulence factor expression by 10%, 20%, 30%, 40%, 50%, 60%, 70%, 80%, 90%, or as much as 100% as compared to untreated bacteria.

*V. cholerae*. There are several characteristics of pathogenic *V. cholerae* that are important determinants of the colonization process. These include adhesins, neuraminidase, motility, chemotaxis and toxin production. If the bacteria are able to survive the gastric secretions and low pH of the stomach, they are well adapted to survival in the small intestine. *V. cholerae* is resistant to bile salts and can penetrate the mucus layer of the small intestine, possibly aided by secretion of neuraminidase and proteases. Specific adherence of *V. cholerae* to the intestinal mucosa is likely mediated by the long filamentous TCP pili which are coregulated with expression of the cholera toxin genes.

As indicated herein, *V. cholerae* produces cholera toxin, which is composed of two A subunits and five B subunits. The B subunits allow binding to a ganglioside ($GM_1$) receptor on the intestinal epithelial cells. The B pentamer must bind to five corresponding $GM_1$ receptors. This binding occurs on lipid rafts, which anchor the toxin to the membrane for endocytosis of the A subunits, thereby trafficking the toxin into the cell and to the basolateral surface where it acts (Lencer (2001) *Am. J. Physiol. Gastrointest. Liver Physiol.* 280:G781-G786). Once internalized, the A subunits proteolytically cleave into A1 and A2 peptides. The A1 peptide ADP-ribosylates a GTP-binding protein, thereby preventing its inactivation. The always active G protein causes adenylate cyclase to continue forming cAMP. This increase in intracellular cAMP blocks absorption of sodium and chloride by microvilli and promotes the secretion of water from the intestinal crypt cells to preserve osmotic balance (Torgersen, et al. (2001) *J. Cell Sci.* 114:3737-3747). This water secretion causes the watery diarrhea with electrolyte concentrations isotonic to plasma. The fluid loss occurs in the duodenum and upper jejunum, with the ileum less affected. The colon is less sensitive to the toxin, and is therefore still able to absorb some fluid. The large volume, however, overwhelms the colon's absorptive capacity.

In addition to *V. cholerae*, the following is a list of some of the bacterial enteric pathogens that express A/X family members that properly align with ToxT. In so far as other pathogens may be identified based upon the structural analysis disclosed herein, the following list is merely illustrative and in no way limits the scope of bacteria that can be targeted by the instant fatty acid compositions.

*Escherichia coli*. There are several pathogenic derivatives of *E. coli*. Several of the most common are as follows. One is Enterohemorrhagic *E. coli* (EHEC), which causes a *Shigella*-like illness and is also known as the hamburger meat *E. coli*. Another is Enteropathogenic *E. coli* (EPEC), which causes persistent diarrhea in children. EPEC expresses a surface appendage termed the bundle forming pilus, or BFP. BFP is required for intestinal colonization by the bacterium. BFP gene expression is activated by the A/X family member PerA that meets alignment criteria described herein. A third example is Enterotoxigenic *E. coli* (ETEC), which expresses a toxin identical to ToxT and causes traveler's diarrhea. ETEC expresses colonization factor adhesions termed CS1 and CS2. The expression of the corresponding genes is activated by an A/X family regulator termed Rns that meets alignment criteria described herein. Similarly, the cof gene cluster, *Longus* gene cluster and CFA/I operon of ETEC also respectively encode regulatory proteins cofS, lngS and CfaD, which regulate the expression of virulence factors. Indeed, CfaD and Rns are fully interchangeable with each other (Bodero, et al. (2007) *J. Bacteriol.* 189:1627-32) and recognize the same DNA binding sites.

*Salmonella. Salmonella* cause 1.4 million cases of gastroenteritis and enteric fever per year in the US and lead all other food borne pathogens as a cause of death. While there are over a thousand serotypes of *Salmonella* that can cause gastroenteritis, *S. enteritidis* (sv. *Typhimurium*) is the leading cause. *S. enteritidis* (sv. *Typhimurium*) infection of mice serves as a model for typhoid fever as the causative agent of this disease only infects humans. As such, this species has served as a model organism for both gastroenteritis and typhoid fever. Most of the genes that encode virulence factors are located in clusters on *salmonella* pathogenicity islands termed SPIs. SPI-1 carries the genes for a type III secretion system (T3SS), the expression of which is critical for virulence. The master regulator of the expression of SPI-1 genes is HilA. The expression of HilA itself is controlled by HilD. HilD is an A/X family member that meets alignment criteria described herein.

*Salmonella typhi* (*S. enterica* sv. *Typhi*) is the leading cause of enteric fever also known as typhoid fever. Typhoid fever is estimated to affect approximately 17 million people annually, causing 600,000 deaths. *S. typhi* is a multi-organ organism, infecting lymphatic tissues, liver, spleen, and bloodstream. *S. typhi* has a gene regulatory network similar to the SPI-1 and regulation of T3SS gene expression in *S. enteritidis* (sv. *Typhimurium*). In the case of *S. typhi* the aligned A/X family member is designated SirC.

*Shigella*. Several *Shigella* species are responsible for the majority of bacillary dysentery that is caused by this organism. *S. dysenteriae* is common in many parts of the world. *S. flexneri* and *S. sonnei* are the most common in the U.S. Most molecular analysis regarding *Shigella* has been performed with *S. flexneri*. This species requires a surface protein, IcsA, to nucleate actin and travel through and between host cells. Expression of the icsA gene is activated by VirF, which meets alignment criteria described herein.

*Bacillus anthracis. Bacillus anthracis* is an aerobic spore-forming bacteria that causes anthrax disease. Livestock may become infected by eating or inhaling anthrax spores. Humans, especially farmers and individuals who work in slaughterhouses, may develop cutaneous anthrax through skin exposure to infected animals. Humans can also get inhalational anthrax by breathing in material contaminated with the bacteria. This bacterium also expresses an AraC family member.

*Listeria*. *Listeria monocytogenes* is a facultative intracellular bacterium that is the causative agent of Listeriosis. It is one of the most virulent food-borne pathogens with 20 to 30 percent of clinical infections resulting in death. *Listeria monocytogenes* also expresses an AraC family member.

*Staphylococcus aureus*. *Staphylococcus aureus* is a facultatively anaerobic, gram-positive coccus and is the most common cause of staph infections. Some strains of *S. aureus*, which produce the exotoxin TSST-1, are the causative agents of toxic shock syndrome, whereas other strains of *S. aureus* also produce an enterotoxin that is the causative agent of *S. aureus* gastroenteritis.

*Yersinia enterocolitica* is a common pathogen of children and adults, with a strong propensity for extraintestinal complications. Gastrointestinal disorders include enterocolitis, particularly in children, and pseudoappendicitis, particularly in young adults. *Y. enterocolitica* virulence factors include outer proteins termed Yops and YadA, which is an adhesin that is essential for colonization. VirF is an A/X family member that meets alignment criteria described herein.

*Yersinia pestis* is the pathogen of human and animals that causes all three main forms of the plague including pneumonic, septicemic and bubonic plagues. Similar to VirF, the *Y. pestis* virulence regulon is controlled by the A/X family member LcrF (Hoe, et al. (1992) *J. Bacteriol.* 174:4275-86).

In addition, *Bacillus anthracia*, the etiologic agent of anthrax; *Brucella abortus*, which causes brucellosis; and *Clostridium botulinum*, the causal agent of botulism, each have an A/X family member that meets alignment criteria described herein.

In so far as ToxT and other A/X regulatory proteins directly regulate the expression of virulence factors, which are involved in pathogenicity, inhibition of A/X regulatory protein activity, and hence virulence factor expression, is useful in the prevention, mitigation, and/or treatment of enteropathogenic bacterial infection. As used herein, the term "bacterial infection" is used to describe the process of adherence and virulence factor production by a pathogenic bacterium that expresses an A/X regulatory protein. For the purposes of the present invention, the term "treatment" or "treating" means any therapeutic intervention in a mammal, preferably a human or any other animal suffering from a enteropathogenic bacterial infection, such that symptoms and bacterial numbers are reduced or eliminated. By way of illustration, it is contemplated that by reducing adhesion of *V. cholerae* to the intestinal mucosa via TCP pili, colonization will be reduced or inhibited, thereby allowing the subject to clear the bacterial infection.

"Prevention" or "preventing" refers to prophylactic treatment, wherein clinical symptom development is delayed or inhibited, e.g., preventing infection from occurring and/or developing to a harmful state.

"Mitigation" or "mitigating" means arresting the development of clinical symptoms, e.g., stopping an ongoing infection to the degree that it is no longer harmful, or providing relief or regression of clinical symptoms, e.g., a decrease in fluid loss resulting from an infection.

Prophylactic or therapeutic treatment involves the administration of an effective amount of a compound of this invention to a subject in need thereof, thereby preventing, mitigating, or treating a bacterial infection. Subjects benefiting from the method of the invention include those having a bacterial infection (e.g., exhibiting signs or symptoms) or those at risk of having a bacterial infection (e.g., a subject exposed to a contaminated food or water source).

The terms "effective amount" means a dosage sufficient to measurably decrease or inhibit virulence gene expression and provide prevention, mitigation and/or treatment of a bacterial infection. In prophylactic or therapeutic applications, preferably the administered dose delays, mitigates, or reduces the signs and/or symptoms of infection in the subject by at least about 20%, more preferably by at least about 40%, even more preferably by at least about 60%, and still more preferably by at least about 80% relative to untreated subjects. The efficacy of a compound can be evaluated in an animal model system that may be predictive of efficacy in preventing, mitigating or treating the disease in humans.

The amount and dosage regimen of the composition of the invention to be administered is determined in the light of various relevant factors including the purpose of administration (e.g., prevention, mitigation or treatment), the age, sex and body weight of an individual subject, and/or the severity of the subject's symptoms. In this respect, the compositions of the invention can be administered under the supervision of a medical specialist, or may be self-administered.

Daily dosage of a composition of the present invention would usually be single or multiple servings per day, e.g., once or twice daily, for acute or chronic use. However, benefit may be derived from dosing regimens that can include consumption on a daily, weekly or monthly basis or any combination thereof. Administration of compositions of the invention, e.g., treatment, could continue over a period of days, weeks, months or years, until an infection has been treated. Optimally, the composition of the invention is consumed at least once a day on a regular basis, to prevent an infection.

The invention is described in greater detail by the following non-limiting examples.

Example 1: Design and Synthesis of Compounds

Based upon the structure of palmitoleic acid, small molecule inhibitors of ToxT were designed. A synthetic method for preparing exemplary compounds of the invention is presented in Scheme 1.

SCHEME 1

1-bromo-8-methyl-naphthalene adipic anhydride

Li or Mg

Figure 2:
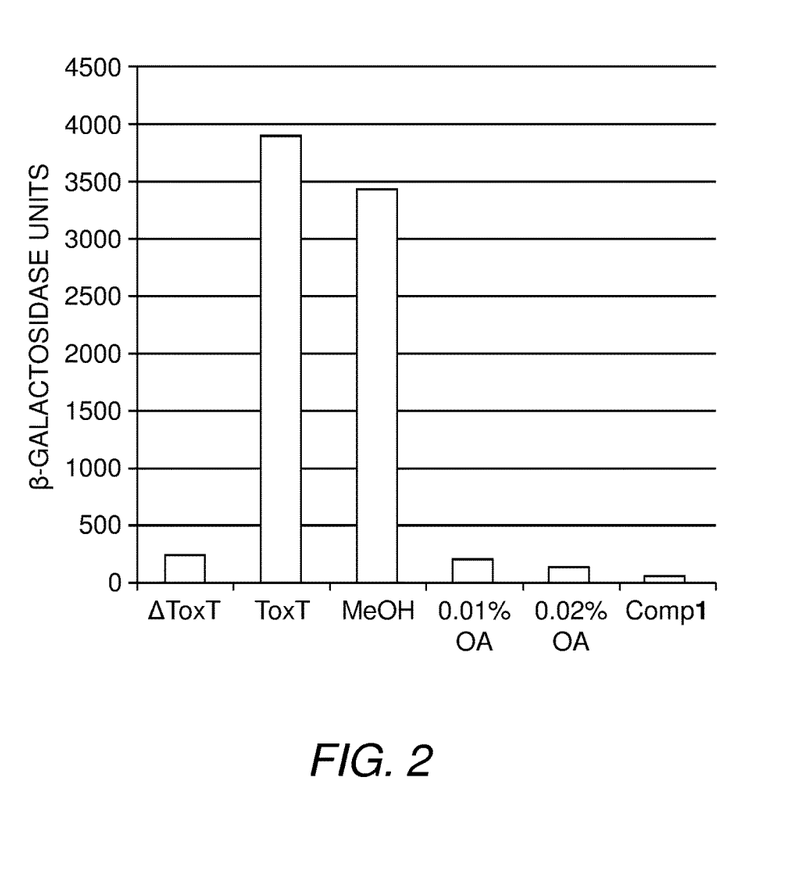

Compound 1 was tested in a reporter assay to determine its effect on inhibiting the activity of ToxT. This analysis indicated that compound 1 effectively inhibited the activity of ToxT as determined in a tcp reporter assay (FIG. 2).

In light of the activity of compound 1, this invention also includes derivatives of compound 1. To modify activity, specificity, and/or bioavailability, additional derivatives of compounds 1-3 can be prepared. For example, by varying the anhydride (or a functionalized dicarboxylic acid), the carbon chain linking the naphthalene ring to the carboxylate head group can be lengthened or shortened. Thus, reaction of 1-bromo-8-methylnaphthalene with glutaric anhydride will afford a compound similar to compounds 1-3 having three carbons between the ketone carbonyl and the carboxylate group. Likewise, carrying out the acylation reaction with pimelic acid anhydride will give a compound similar to compounds 1-3 having five carbons between the ketone carbonyl and the carboxylate group. Accordingly, the acylation reaction can be carried out with any suitable dicarboxylic acid, e.g., malonic, succinic, glutaric, adipic, pimelic or suberic acid/anhydride, to achieve a compound having between 1 and 6 carbons between the ketone carbonyl and the carboxylate group.

Further, the methyl group attached to the naphthalene ring can be substituted with any other alkyl or polar group, either by de novo synthesis from a suitable 2-alkylfuran and 3-bromobenzyne (see synthesis of 1-bromo-8-methylnaphthalene in Scheme 1) or by modification of the methyl group in the final product. For example, appropriate oxidation will convert this methyl group to a carboxylate or to a hydroxyl group. Of note, the synthesis of 1-bromo-8-methylnaphthalene automatically gives the isomeric 1-bromo-5-methylnaphthalene, which provides a set of control compounds isomeric to compounds 1-3.

The aromatic carbonyl ketone group can be readily reduced with sodium borohydride in trifluoroacetic acid (Gribble, et al. (1978) *Synthesis* 763) or other two-step reduction procedures known in the art. The resulting compounds can be further reduced by catalytic hydrogenation to a derivative of compound 3. By adjusting the reduction conditions (e.g., Birch reduction), compounds having one reduced ring (i.e., a tetralin analogue [1,2,3,4-tetrahydronaphthalene]) can be prepared.

As a further derivative, the ketone carbonyl in Compound 1 can be converted to an alkene, so as to "stiffen" the carbon chain.

In certain embodiments, the naphthalene ring is replace with 4-methylindole, which could be deemed an isostere to 8-methylnaphthalene. Introduction of carboxylate chains onto the indole C-3 position is facile as this position is extremely susceptible to electrophilic substitution. Moreover, the indole double bond is readily reduced, providing additional flexibility for polarity of the basic two-ring structure. This is shown in Compound 4.

Similarly, the 8-methylnaphthalene unit can be replaced with the isostere 5-methylquinoline. Once again, the C-4 position of quinoline, like C-3 in indole, is very easily substituted and will provide a ring structure for conversion to derivatives of compound 1 and, by reduction, to derivatives of compound 3. This is shown in compound 5, and, for isoquinoline, compound 6.

What is claimed is:

1. A compound or a hydrate, isomer, or pharmaceutically acceptable salt thereof having the structure:

wherein

R$^1$ is C$_2$-C$_6$ alkyl;

R$^2$ is hydrogen, alkenyl, or oxo;

X is —CHCH—, —NH—, —C=N—, or —N=C—;

when X is —CHCH—, R$^2$ is hydrogen, alkenyl, or oxo; when X is —NH—, —C=N—, or —N=C—, R$^2$ is hydrogen, or oxo;

n is 1-6.

2. The compound of claim 1, wherein X is —NH—, —C=N—, —N=C—.

3. The compound of claim 1, wherein X is —CHCH—.

4. The compound of claim 1, wherein n is 3, 4, or 5.

5. The compound of claim 1, wherein n is 1, 2, 3, 4, or 5.

6. The compound of claim 1 having the structure:

7. The compound of claim 1 having the structure:

8. A pharmaceutical composition comprising the compound of claim 1 in admixture with a pharmaceutically acceptable carrier.

9. A compound selected from the group consisting of:

and hydrates, isomers, or pharmaceutically acceptable salts thereof.

10. A pharmaceutical composition comprising the compound of claim 9 in admixture with a carrier.

11. The compound of claim 1 having the structure:

12. The compound of claim 1 having the structure:

wherein n is 1.

* * * * *

UNITED STATES PATENT AND TRADEMARK OFFICE
CERTIFICATE OF CORRECTION

PATENT NO. : 10,377,716 B2
APPLICATION NO. : 15/785193
DATED : August 13, 2019
INVENTOR(S) : F. Jon Kull et al.

Page 1 of 1

It is certified that error appears in the above-identified patent and that said Letters Patent is hereby corrected as shown below:

In the Specification

At Column 1, Lines 22-25:
"This invention was made with government support under contract numbers AI072661 and AI039654 awarded by the National Institutes of Health. The government has certain rights in the invention."

Should read:
-- This invention was made with government support under grant numbers AI060031, AI072661, AI039654, and AI041558 awarded by the National Institutes of Health. The government has certain rights in the invention. --

Signed and Sealed this
Twenty-eighth Day of January, 2020

Andrei Iancu
*Director of the United States Patent and Trademark Office*